US012806311B2

(12) United States Patent
Hiwatari et al.

(10) Patent No.: US 12,806,311 B2
(45) Date of Patent: Nov. 24, 2026

(54) SHEET OF BIOLOGICAL TISSUE, TUBULAR STRUCTURE OBTAINED FROM SAID SHEET, AND ARTIFICIAL BLOOD VESSEL COMPRISING SAID TUBULAR STRUCTURE

(71) Applicant: ADEKA CORPORATION, Tokyo (JP)

(72) Inventors: Ken-ichiro Hiwatari, Tokyo (JP); Yu Yamaguchi, Tokyo (JP); Takuya Kimura, Tokyo (JP); Akiko Tasaki, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 1055 days.

(21) Appl. No.: 17/851,283

(22) Filed: Jun. 28, 2022

(65) Prior Publication Data

US 2022/0323647 A1 Oct. 13, 2022

Related U.S. Application Data

(62) Division of application No. 15/576,761, filed as application No. PCT/JP2016/066003 on May 31, 2016, now abandoned.

(30) Foreign Application Priority Data

Jun. 2, 2015 (JP) ................................ 2015-111957

(51) Int. Cl.
*A61L 27/36* (2006.01)
*A61F 2/06* (2013.01)
*A61L 27/50* (2006.01)

(52) U.S. Cl.
CPC ............ *A61L 27/3625* (2013.01); *A61F 2/06* (2013.01); *A61L 27/3683* (2013.01);
(Continued)

(58) Field of Classification Search
CPC ......... A61F 2/06–2002/077; A61F 2210/0076; A61F 2230/0069; A61L 27/3625; A61L 27/3683; A61L 27/507
See application file for complete search history.

(56) References Cited

U.S. PATENT DOCUMENTS 4,502,159 A * 3/1985 Woodroof ................ A61F 2/06
600/36
5,817,075 A * 10/1998 Giungo ............. A61B 17/3468
606/166
(Continued)

FOREIGN PATENT DOCUMENTS

CN 102481390 5/2012
JP 3055946 6/2000
(Continued)

OTHER PUBLICATIONS

International Search Report issued Aug. 30, 2016 in corresponding International (PCT) Application No. PCT/JP2016/066003.
(Continued)

*Primary Examiner* — Leslie A Lopez
(74) *Attorney, Agent, or Firm* — Wenderoth, Lind & Ponack, L.L.P.

(57) ABSTRACT

A sheet of biological tissue which includes on at least one side tapered edge portion thinning down in the thickness direction, towards an end thereof, a tubular structure obtained from the sheet, and an artificial blood vessel made up of the tubular structure are provided.

19 Claims, 4 Drawing Sheets

(i) (ii)

(52) U.S. Cl.
CPC ..... *A61L 27/507* (2013.01); *A61F 2210/0076* (2013.01); *A61F 2240/001* (2013.01)

(56) References Cited

U.S. PATENT DOCUMENTS

| | | | |
|---|---|---|---|
| 6,737,053 B1 | 5/2004 | Goh et al. | |
| 2003/0181968 A1* | 9/2003 | Xie ........................... | A61F 2/07 623/1.13 |
| 2006/0257447 A1* | 11/2006 | Hinds ..................... | A61L 27/54 424/569 |
| 2011/0054588 A1 | 3/2011 | Xu et al. | |
| 2012/0035527 A1 | 2/2012 | Tearney et al. | |
| 2012/0296353 A1 | 11/2012 | Wagner et al. | |
| 2013/0123920 A1 | 5/2013 | Sun et al. | |
| 2015/0313731 A1 | 11/2015 | Shinya et al. | |

FOREIGN PATENT DOCUMENTS

| | | |
|---|---|---|
| JP | 2009-254777 | 11/2009 |
| JP | 2013-503696 | 2/2013 |
| WO | 96/26759 | 9/1996 |
| WO | 97/24081 | 7/1997 |
| WO | 2014/109185 | 7/2014 |

OTHER PUBLICATIONS

Extended European Search Report issued Jan. 15, 2019 in corresponding European Patent Application No. 16803329.8.

* cited by examiner (i)

(ii)

SHEET OF BIOLOGICAL TISSUE, TUBULAR STRUCTURE OBTAINED FROM SAID SHEET, AND ARTIFICIAL BLOOD VESSEL COMPRISING SAID TUBULAR STRUCTURE

TECHNICAL FIELD

The present invention relates to a sheet of biological tissue and to a tubular structure obtained from the sheet, and relates to a sheet and a tubular structure that are appropriately used in artificial blood vessels or the like.

BACKGROUND ART

Blood vessel grafts are utilized to construct blood vessels for bypass surgery, and implement the repair or replacement of damaged or morbid blood vessels.

For instance, patients' own blood vessels yield appropriate replacement grafts in atherosclerosis of coronary arteries and peripheral blood vessels, and, for example, one's own internal thoracic artery, radial artery or saphenous vein is used in affected areas each having a diameter smaller than 5 mm. However, invasive collection cannot be avoided when using one's own blood vessel, which accordingly translates into a significant burden on the patient's body and into inevitable variability in the length and quality of the blood vessel, although the variability differs from patient to patient and from case to case. Furthermore, in cases of reoperation, it is impossible to obtain again patients' own blood vessels as they are already in use.

Artificial blood vessels formed from a synthetic resin such as polyester fibers and polytetrafluoroethylene are used, for instance, in revascularization of limb peripheral arteries. However, an artificial blood vessel made from such synthetic resins cannot be used on account of early thrombus formation or intima thickening, in a case where the artificial blood vessel is used in small-diameter blood vessels such as the coronary arteries. In order to prevent blood from clotting in an artificial blood vessel formed from such synthetic resins, the lumen of the artificial blood vessel is covered with vascular endothelial cells of the patient himself, by resorting to tissue engineering techniques. However, the bone marrow of the patient must herein be sampled, cultured, and allowed to graft onto the artificial blood vessel, prior to surgery, which requires preparations in advance. The usefulness of this approach is low in surgery that must be performed in an emergency. Moreover, the endothelial cells that cover the blood vessel lumen peel-off readily, which may give rise to thrombi.

Such being the case, artificial blood vessels have been proposed in which a sheet of a decellularized biological material is formed into a tubular shape, in order to prevent rejection (PTL 1). This artificial blood vessel is formed by rolling a sheet into a tubular shape without any modification. As a result, the edge portion of the sheet juts into the lumen of the tube, in the luminal cross-section, by the extent of the thickness of the sheet, which thus makes the cross-section of the tube not to be circular or elliptical (FIG. 8). When the cross-section of the tubular structure is thus shaped, localized pressure acts on the portion that juts out when blood flows therethrough; as a result, peel-off may occur and thus the pressure resistance of the blood vessel is insufficient. Increasing the thickness of the sheet in order to secure pressure resistance entails poorer handleability during surgery. Moreover, it is considered that platelets and the like adhere to the portion jutting out more easily, which is likely to result in a thrombus.

CITATION LIST

Patent Literature

[PTL 1] WO 2014/109185

SUMMARY OF INVENTION

Technical Problem

Therefore, an object of the present invention is to provide a sheet of biological tissue for obtaining a tubular structure which has excellent processability, pressure resistance and handleability. Another object of the present invention is to provide a tubular structure which has excellent pressure resistance and handleability. Still another object of the present invention is to provide an artificial blood vessel which has excellent pressure resistance and handleability, and in which occurrence of thrombi is suppressed.

Solution to Problem

Specifically, the inventors perfected the present invention as a result of diligent research aimed at solving the above problems.

The present invention is:

(1) a sheet of biological tissue, the sheet including on at least one side tapered edge portion thinning down in the thickness direction, towards an end thereof;

(2) the sheet of biological tissue of (1), wherein the sheet of biological tissue is rectangular or substantially rectangular, and includes on a least one side in the length direction tapered edge portion thinning down in the thickness direction, towards the end;

(3) the sheet of biological tissue of (1) or (2), wherein the angle of the tapered edge lies in a range of 10° to 80°;

(4) the sheet of biological tissue according to any one of (1) to (3), wherein the thickness of the sheet is 500 micrometers or less;

(5) the sheet of biological tissue according to any one of (1) to (4), wherein the tapered edge has a slanting shape on one face of the sheet;

(6) the sheet of biological tissue according to any one of (1) to (5), wherein the biological tissue is an animal blood vessel;

(7) the sheet of biological tissue according to any one of (1) to (6), wherein the sheet of biological tissue is decellularized tissue;

(8) a tubular structure, having a tapered portion of the sheet of biological tissue according to any one of (1) to (7) positioned on the inner side and fixed to an inner wall of the tubular structure;

(9) a tubular structure, obtained after rolling the sheet into a tubular shape and fixing the tapered portion thereof to the inner wall in such a manner that the tapered portion of the sheet of biological tissue according to any one of (1) to (6) is positioned on the inside and then performing decellularization;

(10) the tubular structure according to (8) or (9), wherein at least a part of a wall portion of the tubular structure has a two-layer structure;

(11) the tubular structure according to any one of (8) to (10), wherein the tapered edge portion is adhered and fixed to the inner wall of the tubular structure;

(12) the tubular structure according to any one of (8) to (11), wherein the inner circumference of the tubular structure is 6.0 millimeters or greater and 40 millimeters or less;

(13) an artificial blood vessel, obtained from the tubular structure according to any one of (8) to (12);

(14) a method of using the tubular structure according to any one of (8) to (12) as an artificial blood vessel; and

(15) use of the tubular structure according to any one of (8) to (12), to produce an artificial blood vessel.

Advantageous Effects of Invention

The present invention allows the provision of a sheet of biological tissue for obtaining a tubular structure having excellent pressure resistance and handleability. By an increase in flexibility, a tapered portion becomes firmly adhered and does not peel off or curl readily. Accordingly, the sheet of the present invention exhibits excellent processability. Further, a tubular structure that has excellent pressure resistance and handleability can be provided. An artificial blood vessel can likewise be provided, which exhibits excellent pressure resistance and handleability, and in which occurrence of thrombi is suppressed.

DESCRIPTION OF EMBODIMENTS

Figure 1:
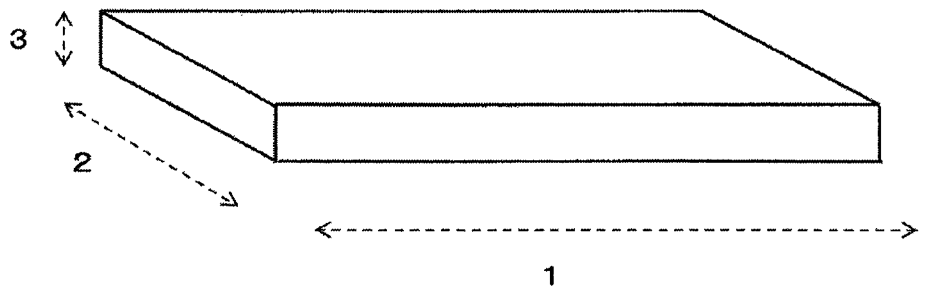
FIG. 1 illustrates a schematic diagram of one embodiment of a rectangular sheet of biological tissue, before taper formation, where dashed line 1 denotes the length direction of the sheet, dashed line 2 denotes the width direction of the sheet, and dashed line 3 denotes the thickness direction of the sheet.

An explanation concerning a sheet of biological tissue (hereafter also "sheet") that can suitably provide the tubular structure of the present invention, and concerning a tubular structure follows next.

Tissue of biological origin (also referred to as "biological tissue") is used as the material of the sheet of the present invention. The term "biological origin" denotes herein "of animal origin", preferably of "vertebrate origin", and yet more preferably to "mammalian biological tissue" or "avian biological tissue", on account of the milder rejection incurred. From the viewpoint of easy availability, the term "biological origin" denotes more preferably biological tissue derived from mammalian livestock, avian livestock, or human tissue. Examples of mammalian livestock include cows, horses, camels, llamas, donkeys, yaks, sheep, pigs, goats, deer, alpacas, dogs, raccoon dogs, weasels, foxes, cats, rabbits, hamsters, guinea pigs, rats, mice, squirrels, raccoons and the like. Examples of avian livestock include parakeets, parrots, chickens, ducks, turkeys, geese, guinea fowl, pheasants, ostriches, quail and the like. Preferred among the foregoing are bovine, porcine, equine or human biological tissues, and yet more preferably, porcine tissue, in terms of safety and easy availability.

As a biological tissue site, a site having an extracellular matrix structure can be used. Examples of such a site are, for instance, tissue from the liver, kidneys, ureters, bladder, urethra, tongue, tonsil, esophagus, stomach, small intestine, colon, anus, pancreas, heart, blood vessels, spleen, lungs, brain, bone, spinal cord, cartilage, testis, uterus, fallopian tubes, ovaries, placenta, cornea, skeletal muscle, tendons, nerves, skin, fascia, pericardium, dura mater, umbilical cord, heart valves, cornea, amniotic membrane, intestinal tract, small intestine submucosa, as well as from other collagen-containing tissues.

Preferred among the foregoing is vascular tissue, for instance from arteries and veins, from the viewpoint of ease of decellularization, easy availability, and handleability and pressure resistance when made into a tubular structure.

Vascular tissue of animal origin is particularly preferred in a case where the tubular structure is used as an artificial blood vessel. Preferred among vascular tissues are arteries, such as the aorta, carotid artery, internal thoracic artery, radial artery, gastro-epiploic artery and the like, from the viewpoint of the characteristics of the artificial blood vessel and in terms of processability; the aorta is more preferred herein by virtue of having sufficient length and thickness and affording excellent processability.

The vascular tissue may be any one or more from among intimal tissue (hereafter also referred to as "intima"), medial tissue (hereafter also referred to as "media") and adventitial tissue (hereafter also referred to as "adventitia"), and preferably the tissue is made up of both intimal tissue and medial tissue, from the viewpoint of pressure resistance, handleability and processability. In this case there may be present tissue originally existing between the intimal tissue and the medial tissue.

When vascular tissue made up of intimal tissue and medial tissue is used, it is preferable to form a tubular structure in such a manner that the inner side of the tube is of intimal tissue.

The shape of the sheet may be arbitrary, but is preferably rectangular (oblong) or substantially rectangular, from the viewpoint of the pressure resistance, handleability and processability of the tubular structure. In the case of a rectangular (oblong) or substantially rectangular sheet, the size of the sheet may be selected as appropriate depending on the size of the tubular structure to be produced, but when made into a tubular structure the length of one side in the length direction (hereafter also referred to as "long side") is ordinarily 10 to 400 millimeters, preferably 20 to 300 millimeters (for instance, dashed arrow 1 in FIG. 1 and FIG. 9), from the viewpoint of pressure resistance and handleability.

Figure 9:
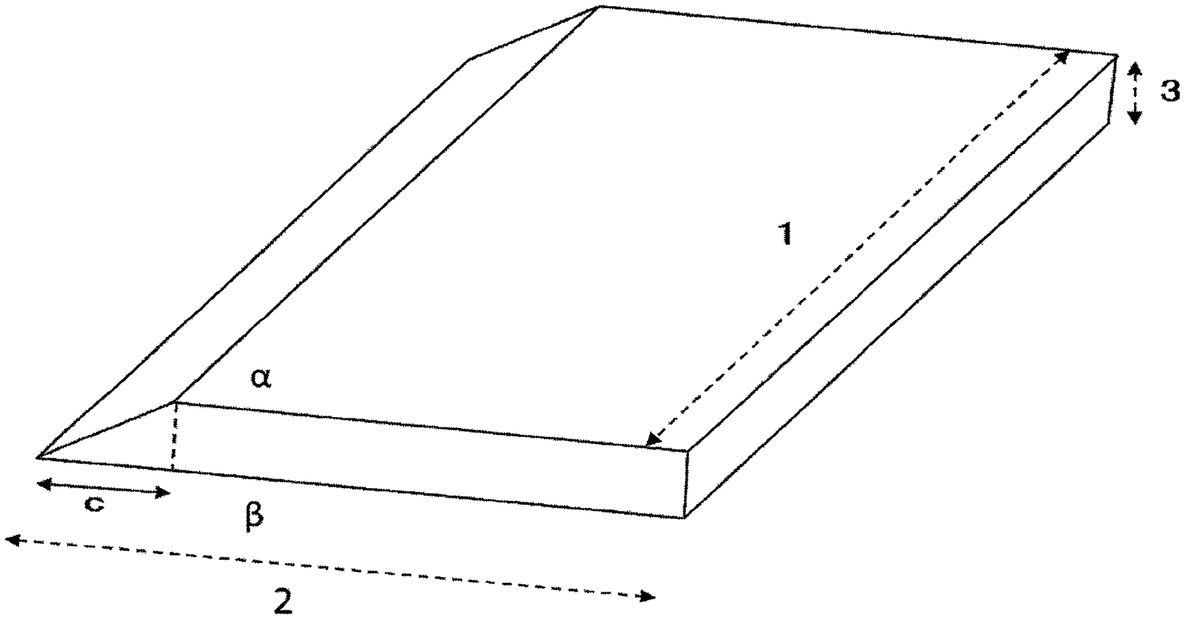
FIG. 9 is a schematic diagram of a sheet of biological tissue in a preferred embodiment of the present invention; a taper is formed on one side in the length direction of the sheet, with an edge portion on one face alone being slanted towards an end thereof; c corresponds to the tapered portion of FIG. 2; more preferably, an $\alpha$ side (upper side) is medial tissue of a blood vessel, and a $\beta$ side (lower side) is intimal tissue of the blood vessel.

Similarly, the length of one side of the sheet in the width direction (hereafter also referred to as "short side") is ordinarily 1.5 to 200 millimeters, preferably 3.0 to 70 millimeters, and more preferably 6.0 to 40 millimeters (for instance, dashed arrow 2 in FIG. 1 and FIG. 9).

The edge portion on at least one side of the sheet of the present invention has a shape (taper) of decreasing thickness towards the end of the edge portion. Typically, the sheet has a shape such as that of portion c in FIG. 9. Specifically, both ends or one end of the cross-section of the sheet have a tapered shape. In the present specification such a shape is referred to as a "taper". The cross-section of the sheet need not be processed linearly. The tapered portion may encompass all edge portions on four sides of the sheet; alternatively, the edge portions on three sides, two sides or one side may be tapered. As described in detail further on, the sheet of the present invention forms a tubular structure by being rolled in the form of a tube in such a manner that the tapered portion lies on the inner side of the tube (luminal side in a case where the sheet is used as an artificial blood vessel).

More preferably, the number of production steps is small, in terms of efficiency in preparing the sheet of the present invention. Accordingly, the taper is preferably present at edge portions on at least two sides of the sheet, more preferably the taper is present at edge portions on two sides of the sheet in the length direction, yet more preferably the taper is present at an edge portion on one side of the sheet, and most preferably, the taper is present at an edge portion on one side in the length direction.

FIG. 1 illustrates a schematic diagram of one embodiment of a sheet of biological tissue, before taper formation.

Figure 2:
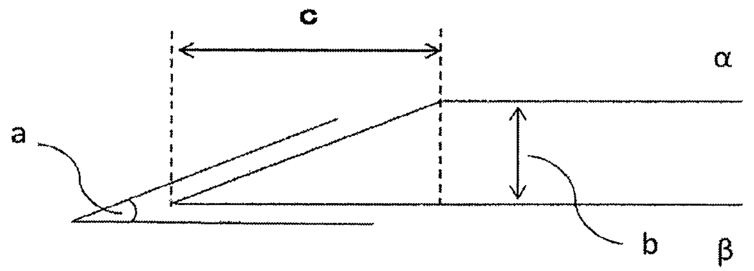
FIG. 2 is a diagram illustrating a cross-section of a tapered portion in a preferred embodiment of the sheet of biological tissue of the present invention, where a denotes the taper angle, b denotes the thickness of the sheet, and c denotes a tapered portion.

FIG. 2 to FIG. 5 illustrate schematic diagrams of the taper at the edge portion of the sheet of the present invention. FIG. 2 to FIG. 5 are partial cross-sectional views in a direction perpendicular to the length direction of the sheet. Herein, the reference symbol a represents the angle of the taper (hereafter also referred to as "taper angle"), and b represents the thickness of the sheet. A portion denoted by c is a tapered portion. FIG. 2 illustrates a part of a cross-sectional view in a direction perpendicular to the length direction of FIG. 1.

Figure 3:
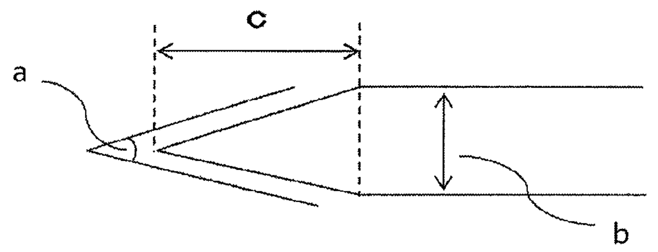
FIG. 3 is a diagram illustrating a cross-section of a tapered portion in another embodiment of the present invention.
Figure 4:
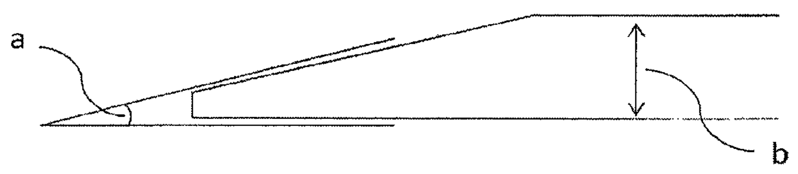
FIG. 4 is a diagram illustrating a cross-section of a tapered portion in yet another embodiment of the present invention.
Figure 5:
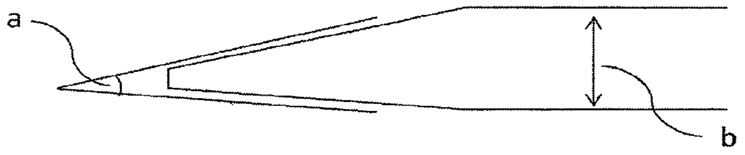
FIG. 5 is a diagram illustrating a cross-section of a tapered portion in still another embodiment of the present invention.

Here, FIG. 2 and FIG. 4 each illustrate a state in which a taper is formed by slanting of an edge portion at one face of the sheet. Further, FIG. 3 and FIG. 5 each illustrate a state in which a taper is formed by slanting of an edge portion at both faces of the sheet.

Ordinarily, the taper angle a is preferably 10° to 80°, more preferably 15° to 70°, still more preferably 20° to 65°, and even more preferably 20° to 55°, from the viewpoint of pressure resistance and handleability of the tubular structure when the sheet is shaped into a tubular structure.

The thickness b of the sheet is preferably 100 to 500 micrometers, more preferably 150 to 400 micrometers, and still more preferably 200 to 300 micrometers, from the viewpoint of pressure resistance and handleability when made into a tubular structure. A thickness beyond 500 micrometers is too large for the sheet to be processed, and is inappropriate for producing a small-diameter tubular structure.

The sheet thickness b corresponds to the thickness of the sheet in FIG. 1 and FIG. 9 (denoted by dashed arrow 3).

From the viewpoint of pressure resistance, handleability and processability of the taper shape, the cross-section of the tapered portion such as those of FIG. 2 and FIG. 3 is preferably a triangular shape (for instance, a right triangle shape or an isosceles triangle shape), or substantially triangular shape (for instance, substantially a right triangle shape or substantially an isosceles triangle shape); a taper cross-section such as that of c in FIG. 2 is in particular preferably a right triangle shape or substantially a right triangle shape. FIG. 2 illustrates an instance where the slant of the edge portion on one face of the sheet reaches the other face. In FIG. 2, the tapered portion is preferably formed so that an α side constitutes ultimately the outer wall side of the tubular structure. That is, the edge portion of the sheet is processed (for instance by cutting) so that a taper is formed, in proportion to the taper width, inward from an end of a face, which is to constitute the outer wall of the tubular structure, up to an end portion of a face, which is to constitute the inner wall.

Any means can be used, without particular limitations, to form the taper at the edge portion of the sheet of the present invention, and, for instance, cutting processing may be carried out. Known tools may be used as tools utilized for cutting; examples thereof include cutters, razors, scalpels, ultrasonic cutters, microtomes and the like, without particular limitations.

Figure 6:
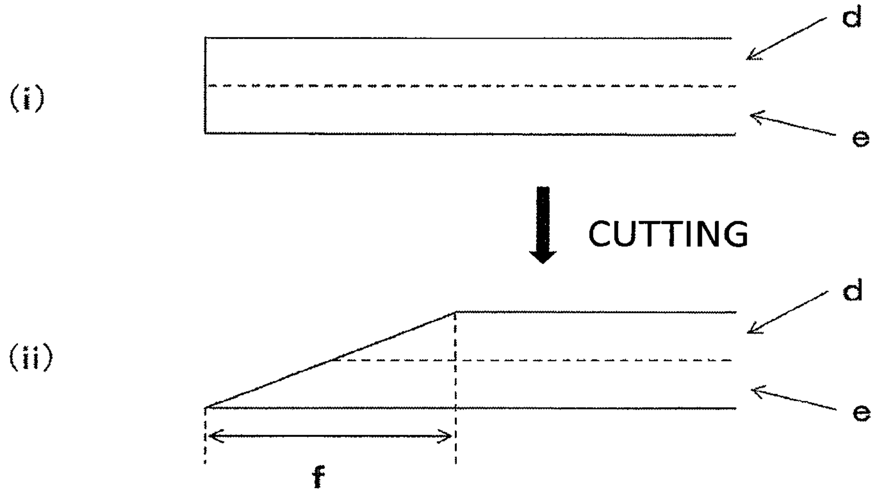
FIG. 6(*i*) is a diagram illustrating a part (cross-section of an edge portion) of a sheet of biological tissue made up mainly of medial tissue and intimal tissue of a blood vessel, before formation of a tapered portion, and FIG. 6(*ii*) is a diagram illustrating a tapered portion formed at the edge portion of the sheet by cutting.

As regards taper length (for instance, reference symbol f in FIG. 6(*ii*)), when the tubular structure is made, a tapered portion is prepared such that the proportion with respect to the inner circumference is preferably 0.01° to 100°, more preferably 0.1% to 50% and still more preferably 0.15% to 35%.

The shape of the tapered portion of the sheet of the present invention is not particularly limited, and the cut surface after being processed may be a flat surface or a curved surface, and may partially have an irregular or jagged shape such as that of a saw blade. Preferably, however, all the cut surfaces after cutting are flat surfaces, if processing efficiency is taken into consideration.

In one preferred embodiment of the sheet of the present invention, a sheet of decellularized tissue of biological origin obtained from an animal blood vessel may be used. This sheet of biological tissue is mainly made up of medial tissue and intimal tissue. FIG. 6(*i*) illustrates a sheet of biological tissue in this preferred embodiment. The dashed line in the figure denotes a boundary, with a reference symbol d denoting medial tissue while e denotes intimal tissue. Cutting to yield a tubular structure involves preferably cutting from the medial tissue side, so that a tip of the taper is formed on the bottom side of the intimal tissue (FIG. 6(*ii*)).

In terms of making processing easier it suffices to place the blade of the cutting tool at a specific position on the medial tissue side of the sheet, on the central portion side from the end, and to drive the blade obliquely with respect to the end portion of the bottom side of the intimal tissue. As a result, it becomes possible to thin down the edge portion on one side of the sheet while imparting an acute-angle taper to the cross-section of that edge portion. The present invention is not limited to the above method, and any method may be employed so long as a similar shape can be obtained.

Processing to form the taper in the sheet is preferably carried out before rolling the sheet into a tubular shape, from the viewpoint of processability, but may be carried out after rolling the sheet into a tubular shape.

The sheet of biological tissue of the present invention is preferably subjected to a decellularization treatment. Decellularization will be explained in detail next.

Decellularization is a treatment for removing highly antigenic components, such as cells and nucleic acid components, from tissue sampled from an animal. This allows the suppression of rejection that occurs when the tissue is used as transplant tissue in a living body.

The decellularization method in the present invention is not particularly limited, and a conventional known method can be employed. Examples of decellularization treatments include physical agitation, ultrasonic processing, freeze-thaw methods, high hydrostatic pressure methods, hypertonic solution/hypotonic solution methods, treatments using surfactants such as anionic surfactants or nonionic surfactants, enzymatic treatment by proteolytic enzymes, nucleolytic enzymes and the like, as well as treatments using alcohol solvents. The foregoing may be implemented in combinations of two or more thereof.

A method including a high hydrostatic pressure method is preferably used in the present invention since such a method allows decellularization with favorable efficiency while preserving the mechanical strength of structural proteins, and also in terms of hemocompatibility.

The decellularization treatment may be performed before making the biological tissue into a sheet, or after shaping the biological tissue as a sheet, or before cutting for imparting a taper to a sheet end, or after cutting, or after formation of the sheet into a tubular structure. Preferably, the decellularization treatment is carried out before formation of the tubular structure, and more preferably after formation of the biological tissue into a sheet shape, from the viewpoint of processability and ease of decellularization.

Figure 7:
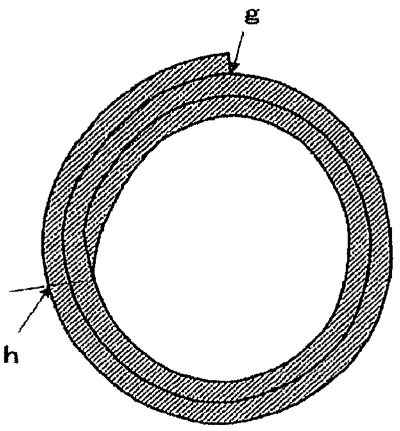
FIG. 7(*i*) is a diagram illustrating a front cross-section of a tubular structure in one embodiment of the present invention, and FIG. 7(*ii*) is a diagram illustrating a front cross-section of a tubular structure in another embodiment of the present invention.
Figure 7:
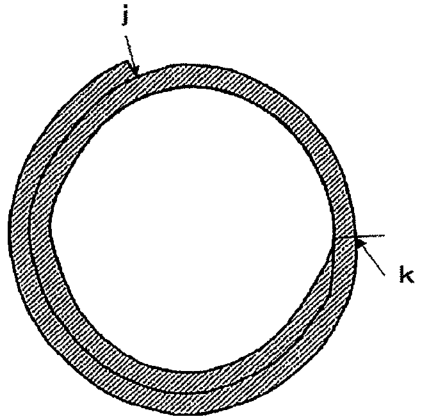

The tubular structure of the present invention is formed from the sheet of biological tissue—material—of the present invention. Specifically, the tubular structure is obtained by rolling the sheet of the present invention into a tubular shape in such a manner that the tapered portion of the sheet is positioned on the inner side (luminal side). FIG. 7 illustrates preferred embodiments of the tubular structure of the present invention.

Figure 8:
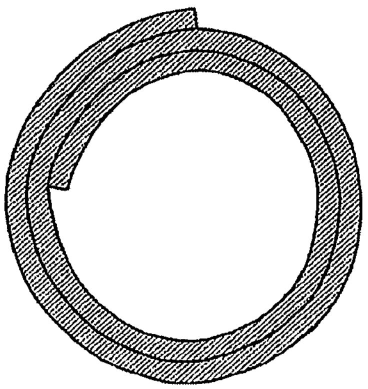
FIG. 8 is a diagram illustrating a front cross-section of a tubular structure used, for instance, in a conventional artificial blood vessel.

If a tubular structure with no taper at the edge portion of the sheet is formed, the edge portion of the sheet will protrude, by the extent of the thickness of the sheet, into the lumen of the tube (FIG. 8). In a case where, for instance, the tubular structure is used as an artificial blood vessel, localized pressure acts on that protrusion when blood flows therethrough; as a result, peel-off may occur, and the pressure resistance of the sheet as an artificial blood vessel may be insufficient.

In contrast, when forming a tubular body of the sheet of the present invention in such a manner that the tapered portion of the sheet lies on the inner side (luminal side) of the tube, there is no portion jutting out, which is ascribed to the thickness of the edge portion of the sheet, in the cross-section of the tubular body, and the cross-section of the tubular body has a circular, elliptical, substantially circular or substantially elliptical shape (see for instance FIG. 7). As a result, excellent pressure resistance is obtained as pressure is exerted uniformly within the tube, and a flow of fluid such as blood exhibits smooth flow, without peel-off of the fixing portion of the tubular body. Further, since there is no portion jutting out at the initial site of rolling, the tubular structure accordingly has uniform flexibility and also superior handleability.

Due to the superior pressure resistance, it is not necessary to increase the thickness of the sheet itself to achieve pressure resistance, and hence excellent handleability is exhibited.

From the viewpoint of pressure resistance, a part of the wall portion that forms the tubular structure of the present invention preferably has a two-layer structure. Embodiments where a part of the wall portion that forms the tubular structure is a two-layer structure include a tubular structure having a two-layer structure and a three-layer structure as the wall portion (FIG. 7(*i*)), a tubular structure in which the entire wall portion is a two-layer structure, and a tubular structure having a single-layer structure and a two-layer structure as the wall portion (for instance, FIG. 7(*ii*)).

The length of the two-layer structure portion in the tubular structure having a two-layer structure and a three-layer structure as the wall portion (distance on the outer wall from point g on the outer wall clockwise up to point h, in FIG. 7(*i*)) is preferably 0% or more, more preferably 50% or more, and still more preferably 80% or more of the length of the outer circumference.

The point h is a point at which a line stretching vertically from the tip of the tapered portion intersects the outer wall portion.

Further, the length of the outer circumference denotes herein the length of the outer wall portion of the tubular structure, taking one arbitrary point of the tubular structure as the starting point and end point. For instance, the length of the outer circumference in FIG. 7(*i*) denotes the length of the outer wall portion of the tubular structure, taking g as the starting point and end point.

The length of a single-layer structure portion in a tubular structure having a single-layer structure and a two-layer structure as a wall portion (in FIG. 7(*ii*), a distance on the outer wall from point j on the outer wall, clockwise up to point k) is preferably less than 100%, more preferably 50% or less, and still more preferably 20% or less of the length of the outer circumference.

Point k is a point at which a line stretching vertically from the tip of the tapered portion intersects the outer wall portion.

Further, the length of the outer circumference denotes herein the length of the outer wall portion of the tubular structure, taking one arbitrary point of the tubular structure as the starting point and end point. For instance, the length of the outer circumference in FIG. 7(*ii*) denotes the length of the outer wall portion of the tubular structure, taking j as the starting point and end point.

The tubular structure of the present invention is not limited to the tubular structure illustrated in FIG. 7, and encompasses also a tubular structure having a wall portion of four- or higher-layered structure.

The front cross-section of the tubular structure of the present invention is circular, substantially circular, elliptical or substantially elliptical, as illustrated in FIGS. 7(*i*), 7(*ii*), and is highly flexible, and the shape of the tubular structure can be deformed in accordance with intended use. Ordinarily, the inner circumference of the front cross-section is preferably 1.5 to 200 millimeters, more preferably 3.0 to 70 millimeters, and still more preferably 6.0 to 40 millimeters.

A method for producing the tubular structure of the present invention will be explained next. The present invention is not limited to the production method below, which is exemplary in nature.

The tubular structure of the present invention is produced out of a sheet of biological tissue, for instance in accordance with the production method having steps (1) through (4) below:

(1) a step of forming tissue of biological origin into a sheet shape;
(2) a step of decellularizing the tissue of biological origin;
(3) a step of processing an edge portion on at least one side of the sheet to process the edge portion to be thinner and tapered; and
(4) a step of forming a tubular structure by rolling the sheet.

The order of implementing the steps from (1) to (4) above is not particularly limited, but is preferably (1), (2), (3), (4), or (1), (3), (2), (4), or (1), (3), (4), (2), or (2), (1), (3), (4), and more preferably is (1), (2), (3), (4) or (1), (3), (2), (4) from the viewpoint of easiness of processability.

In (4) above, rolling of the sheet of biological tissue of the present invention yields a tubular shape such that the tapered portion of the sheet is positioned on the inner side (luminal side) of the tubular body. As in c of FIG. 2, the taper cross-sectional view has preferably a right triangle shape or substantially right triangle shape.

Both the surface on the α side and the surface of the β side in FIG. 2 and FIG. 9 can constitute the inner surface of the tubular structure, but preferably the tubular structure is formed by rolling of the tube so that the face on the β side constitutes the inner surface of the tubular structure.

In a case where the sheet of the present invention is rectangular or substantially rectangular, the tube is preferably rolled in such a manner that the sides of the sheet in the length direction yield the length direction of the tubular structure, from the viewpoint of processability.

As one embodiment of formation of the tubular structure, the tubular structure can be formed by winding the sheet on a core member. Concerning the outer circumference and the length of the core member, various types of core members can be selected without limitation to material thereof, depending on the intended inner circumference and the length the tubular structure. The outer circumference of the core member to be used corresponds substantially to the inner circumference of the tubular structure, and a core member may be selected as appropriate in accordance with the intended inner circumference of the tubular structure.

Examples of the core member include, without particular limitations, tubes or cylindrical bars made of polytetrafluoroethylene (PTFE), polyurethane (PU) or a stainless steel material (SUS).

The tubular structure of the present invention can be formed by partially stitching the sheet, or by bonding of part of the sheet using an adhesive, or by resorting to both of the foregoing. Bonding with use of an adhesive is preferable from the viewpoint of processability. Therefore, the tapered portion of the sheet can be fixed to the inner wall of the tubular structure by means of, for instance, stitching or adhesive bonding.

Conventionally used adhesives for biological tissue may be used herein as the adhesive to be utilized, and examples include fibrin glue, cyanoacrylate-based polymerizable adhesives, and gelatin glues resulting from cross-linking of gelatin and resorcinol by formalin, and fibrin glue is preferred from the viewpoint of pressure resistance. Fibrin glue denotes herein a formulation in which pasty clots formed through the action of the enzyme thrombin on fibrinogen are utilized, for instance, in tissue closure, adhesion in organ damage and hemostasis.

The site at which the adhesive is to be applied is not particularly limited, provided that the adhesive allows bonding of the sheet so as to form the tubular structure. Preferably, however, the adhesive is applied so that no adhesive is present on the inner wall surface of the tubular structure. This is because the adhesive may give rise to some adverse effects when coming into contact with a substance passing through the interior (lumen) of the tubular structure. Further, it is necessary to achieve bonding so that the cross-section of the tubular structure, such as those of FIGS. 7(*i*), 7(*ii*) is circular, substantially circular, elliptical or substantially elliptical, by sufficiently coating the tapered portion with the adhesive. This is because when bonding of the tapered portion is insufficient, pressure resistance at the affected portion may be impaired and the desired tubular structure may fail to be obtained.

For instance, in FIG. 2 and FIG. 9, the tubular structure can be prepared by applying the adhesive onto the entire α-side surface of the sheet, followed by bonding together with the β-side surface of the sheet. Further, the α-side surface and the β-side surface of the sheet may be bonded together, while being rolled in a tubular shape, by applying the adhesive only at a portion at which the α-side surface is to be bonded to the β-side surface. In this case the adhesive is not applied onto a portion, which is to form the outer wall surface of the tubular structure, on the α-side surface of the sheet.

The tubular structure of the present invention can be used as a tubular graft of biological tissue. The tubular structure of the present invention can be used in blood vessels, ureters, the trachea, lymph ducts and the like, and particularly preferably in artificial blood vessels.

The tubular structure of the present invention has excellent pressure resistance. In particular when the tubular structure of the present invention is used in artificial blood vessels, the pressure resistance is preferably 300 mmHg or higher, and more preferably 400 mmHg or higher.

The tubular structure of the present invention exhibits excellent handleability, for instance, during surgery.

EXAMPLES

Examples of the present invention will be explained in detail next, but the present invention is not limited to these examples.

Example 1: Production of Tubular Structure No. 1

(Sheet Formation Step, Decellularization Step)

A porcine aorta was purchased from a slaughterhouse, and was transported at 4° C. The adventitia was completely stripped off the aorta, which was then cut open. The aorta thus cut open was then cut out to a substantially rectangular shape having a length of 170 millimeters and a width of 27 millimeters. The obtained sheet was subjected to a high hydrostatic pressure treatment for 15 minutes at 100 MPa in a high pressure processing device for research and development (Dr. CHEF, by Kobe Steel, Ltd.), using saline as a medium. The treated sheet was shaken for 96 hours at 4° C. in saline containing 20 ppm of the nucleolytic enzyme DNase, followed by a treatment for 72 hours at 4° C. in 80% ethanol, and was lastly washed for 2 hours at 4° C. in saline, to yield a decellularized porcine aorta sheet.

<Tip Processing Step>

The thickness of the decellularized porcine aorta sheet thus obtained was 258 micrometers. An edge portion of the sheet on one side in the length direction was cut using a blade (SH35W, by Feather Safety Razor Co., Ltd.) from the medial tissue side towards the intimal tissue side while adjusting the incidence angle of the blade, in such a manner that the cross-section of the edge portion of the sheet exhibited the shape in FIG. 6(*ii*).

Tabularization Step

The biological adhesive fibrin glue was applied to the cut surface and to the surface on the medial tissue side of the sheet thus obtained by cutting, and the sheet was wound on a core in the form of a PTFE tube having an outer diameter of 3.0 millimeters, with pressing for 5 minutes to form a tubular structure, in such a manner that the intimal tissue of the processed sheet yielded the inner side in formation of the tubular structure. By immersing the same in saline, removing the PTFE tube of the core member, and cutting both ends to yield a length of 120 millimeters, a tubular structure No. 1 of the present invention was produced.

The obtained tubular structure No. 1 was cut in a direction perpendicular to the length direction, the cut surface was observed, and the taper angle and length of the tapered portion at the cut edge, where rolling of the tube started (tapered portion, hereafter also referred to as "cut end"), were measured using an inverted microscope (ECLIPSE Ti, by Nikon Corporation). The results are given in Table 1.

In a pressure resistance test carried out in the <Pressure resistance test method> below, the obtained tubular structure was used. The results are given in Table 1.

In a test of handleability, carried out in the <Handling test method> below, the obtained tubular structure was also used. The results are given in Table 1.

Example 2: Production of Tubular Structure No. 2

A tubular structure No. 2 of the present invention was obtained in accordance with the same procedure as in Example 1, but herein the thickness of the decellularized porcine aorta sheet was 217 micrometers, and the incidence angle of the blade was adjusted to modify the taper angle during formation of the tapered portion. The taper angle of the obtained tubular structure No. 2 was measured in the same way as in Example 1, and a pressure resistance test and a handleability test were also carried out. The results are given in Table 1.

Example 3: Production of Tubular Structure No. 3

A tubular structure No. 3 of the present invention was obtained in accordance with the same procedure as in Example 1, but herein the thickness of the decellularized porcine aorta sheet was 275 micrometers, and the incidence angle of the blade was adjusted to modify the taper angle during formation of the tapered portion. The taper angle of the obtained tubular structure No. 3 was measured in the same way as in Example 1, and a pressure resistance test and a handleability test were also carried out. The results are given in Table 1.

Example 4: Production of Tubular Structure No. 4

A tubular structure No. 4 of the present invention was obtained in accordance with the same procedure as in Example 1, but herein the thickness of the decellularized porcine aorta sheet was 173 micrometers, and the incidence angle of the blade was adjusted to modify the taper angle during processing of the edge portion. The taper angle of the obtained tubular structure No. 4 was measured in the same way as in Example 1, and a pressure resistance test and a handleability test were also carried out. The results are given in Table 1.

Example 5: Production of Tubular Structure No. 5

A tubular structure No. 5 of the present invention was obtained in accordance with the same procedure as in Example 1, but herein the thickness of the decellularized porcine aorta sheet was 276 micrometers, and the incidence angle of the blade was adjusted to modify the taper angle during formation of the tapered portion. The taper angle of the obtained tubular structure No. 5 was measured in the same way as in Example 1, and a pressure resistance test and a handleability test were also carried out. The results are given in Table 1.

Example 6: Production of Tubular Structure No. 6

A tubular structure No. 6 of the present invention was obtained in accordance with the same procedure as in Example 1, but herein the thickness of the decellularized porcine aorta sheet was 291 micrometers, and the incidence angle of the blade was adjusted to modify the taper angle during formation of the tapered portion. The taper angle of the obtained tubular structure No. 6 was measured in the same way as in Example 1, and a pressure resistance test and a handleability test were also carried out. The results are given in Table 1.

Example 7: Production of Tubular Structure No. 7

A tubular structure No. 7 of the present invention was obtained in accordance with the same procedure as in Example 1, but herein the thickness of the decellularized porcine aorta sheet was 202 micrometers, and the incidence angle of the blade was adjusted to modify the taper angle during formation of the tapered portion. The taper angle of the obtained tubular structure No. 7 was measured in the same way as in Example 1, and a pressure resistance test and a handleability test were also carried out. The results are given in Table 1.

Example 8: Production of Tubular Structure No. 8

A tubular structure No. 8 of the present invention was obtained in accordance with the same procedure as in Example 1, but herein the thickness of the decellularized porcine aorta sheet was 660 micrometers, and the incidence angle of the blade was adjusted to modify the taper angle during formation of the tapered portion. The taper angle of the obtained tubular structure No. 8 was measured in the same way as in Example 1, and a pressure resistance test and a handleability test were also carried out. The results are given in Table 1.

Comparative Example 1: Production of Comparative Tubular Structure No. C1

A decellularized porcine aorta sheet was obtained by performing a decellularization step in the same way as in Example 1, using a porcine aorta.

The obtained decellularized porcine aorta sheet was cut out to a substantially rectangular shape having a length of 170 millimeters and a width of 27 millimeters. The thickness of the sheet was 255 micrometers.

One side of the sheet in the length direction was cut using a blade, from the medial tissue side towards the intimal tissue side, while adjusting the incidence angle of the blade, to process the sheet to a substantially rectangular shape in which the shape of the cut surface perpendicularly intersects the bottom face of the sheet. Other than this, comparative tubular structure No. C1 was obtained in the same way as in Example 1. The taper angle of the cut end was measured in the same way as in Example 1. The results are given in Table 1. A pressure resistance test and a handleability test were also carried out, in the same way as in Example 1. The results are given in Table 1.

Comparative Example 2: Production of Comparative Tubular Structure No. C2

A decellularized porcine aorta sheet was obtained by performing a decellularization step in the same way as in Example 1, using a porcine aorta.

The obtained decellularized porcine aorta sheet was cut out to a substantially rectangular shape having a length of 170 millimeters and a width of 27 millimeters. The thickness of the sheet was 600 micrometers.

One side of the sheet in the length direction was cut using a blade, from the medial tissue side towards the intimal tissue side, while adjusting the incidence angle of the blade, to process the sheet to a substantially rectangular shape in which the shape of the cut surface intersects perpendicularly the bottom face of the sheet. Other than this, production of the comparative tubular structure No. C2 was attempted in the same way as in Example 1, but no tubular structure could be obtained. It was not possible to obtain a tubular shape on account of the significant thickness of the sheet and due to the fact that no tapering was performed.

<Pressure Resistance Test Method>

A syringe pump (YSP-101, by YMC Co., Ltd.) was connected to one end of each of the obtained tubular structures, via a silicone tube, and the other end was plugged by having a pressure gauge connected thereto. Saline was fed from the syringe, maintaining states respectively for 30 seconds each time pressure was increased by 10 mmHg, while checking the occurrence of breakage or leakage of saline from the tube. Pressure was continuously increased and the pressure immediately preceding observation of saline leakage or breakage was taken as the pressure resistance of the tube. It is found that the higher the pressure, the better the pressure resistance is.

<Handling Test Method>

Each of the obtained tubular structures was pinched at both ends with tweezers, the tubular structures were bent 180° 50 times by so as to bring the two ends in contact with each other with the central portion of the tubular structure as a fulcrum, and the state of the tubular structure after the test was observed. A tubular structure with no change of state from before the test was evaluated as favorable, while the tubular structure exhibiting damage on account of adhesive peel-off or on account of frayed openings was evaluated as defective. Slight peeling at the bonded portion and slight fraying at openings were given an intermediate rating, and were evaluated as admissible.

TABLE 1

| | Tubular structure No. | Taper angle | Taper length | Sheet thickness | Pressure resistance | Handleability |
|---|---|---|---|---|---|---|
| Example 1 | No. 1 | 80° | 45 μm | 258 μm | 300 mmHg | Good |
| Example 2 | No. 2 | 62° | 115 μm | 217 μm | 330 mmHg | Good |
| Example 3 | No. 3 | 52° | 214 μm | 275 μm | 420 mmHg | Good |
| Example 4 | No. 4 | 47° | 161 μm | 173 μm | 410 mmHg | Good |
| Example 5 | No. 5 | 40° | 328 μm | 276 μm | 410 mmHg | Good |
| Example 6 | No. 6 | 35° | 415 μm | 291 μm | 400 mmHg | Good |
| Example 7 | No. 7 | 27° | 396 μm | 202 μm | 460 mmHg | Good |
| Example 8 | No. 8 | 41° | 759 μm | 660 μm | 410 mmHg | Admissible |
| Comp. Ex. 1 | No. C1 | 90° | 0 μm | 255 μm | 120 mmHg | Admissible |
| Comp. Ex. 2 | No. C2 | 90° | 0 μm | 600 μm | Could not be produced | Untested |

The results from the examples and comparative examples reveal that No. 1 to No. 7 exhibit particularly superior pressure resistance and handleability. Accordingly, the tubular structure of the present invention is capable of withstanding blood pressure, as required in a case where the tubular structure is used in an artificial blood vessel. From the viewpoint of handleability as well, the tubular structure makes it easier to perform vascular grafting surgery. Further, No. 8 as well had excellent pressure resistance and exhibited handleability.

By contrast, Comparative Tubular Structure No. C1 was found to have admissible handleability but poor pressure resistance. The thickness in Comparative Tubular Structure No. C2 was substantial, and as no tapering was carried out, a tubular structure could not be obtained.

REFERENCE SIGNS LIST

Dashed arrow 1 Sheet length direction
Dashed arrow 2 Sheet width direction
Dashed arrow 3 Sheet thickness direction;
a Taper angle
b Sheet thickness
c Tapered portion
d Medial tissue
e Intimal tissue f Length of tapered portion
g, h End point of two-layer structure portion
j, k End point of single-layer structure portion

The invention claimed is:

1. A tubular structure comprised of a rectangular or substantially rectangular sheet of biological tissue,
- wherein the sheet of biological tissue comprises on at least one side a tapered edge portion thinning down in a thickness direction, towards an end thereof,
- wherein the tapered edge portion of the sheet of biological tissue is positioned on an inner side and fixed to an inner wall of the tubular structure by applying fibrin glue, and
- wherein an angle of the tapered edge is in a range of 27° to 52°.

2. The tubular structure according to claim 1, wherein a thickness of the sheet is 173 to 660 micrometers.

3. The tubular structure according to claim 2, wherein the at least one side of the sheet is in a length direction.

4. The tubular structure according to claim 3, wherein a length of the at least one side in the length direction of the sheet is 10 to 400 millimeters and a length of one side in a width direction of the sheet is 1.5 to 200 millimeters.

5. The tubular structure according to claim 1, wherein the tapered edge has a slanting shape on one face of the sheet.

6. The tubular structure according to claim 1, wherein a tissue material of the biological tissue is an animal blood vessel.

7. The tubular structure according to claim 1, wherein the sheet of biological tissue is decellularized tissue.

8. The tubular structure according to claim 1, wherein at least a part of a wall portion of the tubular structure has a two-layer structure.

9. The tubular structure according to claim 1, wherein the tapered edge portion is adhered and fixed to the inner wall of the tubular structure.

10. The tubular structure according to claim 1, wherein an inner circumference of the tubular structure is 6.0 millimeters or greater and 40 millimeters or less.

11. The tubular structure according to claim 1, having a pressure resistance of 400 mmHg or higher.

12. A tubular structure, obtained by rolling a rectangular or substantially rectangular sheet of biological tissue having a tapered edge portion into a tubular shape and fixing the tapered edge portion to an inner wall of the tubular structure by applying fibrin glue in such a manner that the tapered edge portion of the sheet of biological tissue is positioned on an inner side and then performing decellularization on the sheet of biological tissue,
- wherein the sheet includes on at least one side the tapered edge portion thinning down in a thickness direction towards an end thereof,
- wherein a thickness of the sheet is 173 to 660 micrometers,
- wherein the at least one side of the sheet is in a length direction,
- wherein an angle of the tapered edge is in a range of 27° to 52°,
- wherein a length of the at least one side in the length direction of the sheet is 10 to 400 millimeters and a length of one side in a width direction of the sheet is 1.5 to 200 millimeters.

13. The tubular structure according to claim 12, wherein the tapered edge has a slanting shape on one face of the sheet.

14. The tubular structure according to claim 12, wherein a tissue material of the biological tissue is an animal blood vessel.

15. The tubular structure according to claim 12, wherein at least a part of a wall portion of the tubular structure has a two-layer structure.

16. The tubular structure according to claim 12, wherein an inner circumference of the tubular structure is 6.0 millimeters or greater and 40 millimeters or less.

17. The tubular structure according to claim 12, having a pressure resistance of 400 mmHg or higher.

18. An artificial blood vessel comprising the tubular structure of claim 1.

19. An artificial blood vessel comprising the tubular structure of claim 12.

* * * * *